US012082773B2

(12) United States Patent
Mizoguchi

(10) Patent No.: US 12,082,773 B2
(45) Date of Patent: Sep. 10, 2024

(54) CONTROL DEVICE, ENDOSCOPE, AND CONTROL METHOD

(71) Applicant: OLYMPUS CORPORATION, Hachioji (JP)

(72) Inventor: Hideaki Mizoguchi, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 203 days.

(21) Appl. No.: 17/895,160

(22) Filed: Aug. 25, 2022

(65) Prior Publication Data

US 2022/0409015 A1 Dec. 29, 2022

Related U.S. Application Data

(63) Continuation of application No. PCT/JP2020/007780, filed on Feb. 26, 2020.

(51) Int. Cl.
*A61B 1/00* (2006.01)
*A61B 1/045* (2006.01)
(Continued)

(52) U.S. Cl.
CPC ...... *A61B 1/00027* (2013.01); *G02B 23/2484* (2013.01); *H02J 4/00* (2013.01);
(Continued)

(58) Field of Classification Search
CPC ............ A61B 1/00025; A61B 1/00027; A61B 1/00032; A61B 1/04; A61B 1/042;
(Continued)

(56) References Cited

U.S. PATENT DOCUMENTS

2015/0138328 A1* 5/2015 Yokohama ............. A61B 1/045 348/65
2015/0280550 A1* 10/2015 Minakuchi ......... G02B 23/2484 323/234
2016/0295141 A1* 10/2016 Sone ....................... H04N 7/18

FOREIGN PATENT DOCUMENTS

JP 2008-161427 A 7/2008
JP 2010-88656 A 4/2010
(Continued)

OTHER PUBLICATIONS

International Search Report dated Apr. 28, 2020, issued in counterpart International Application No. PCT/JP2020/007780 (3 pages).

*Primary Examiner* — Twyler L Haskins
*Assistant Examiner* — Akshay Trehan
(74) *Attorney, Agent, or Firm* — WHDA, LLP

(57) ABSTRACT

A control device includes: a power source configured to supply a predetermined power-supply voltage to an imaging element; a voltage detector configured to detect an output voltage value of the power-supply voltage supplied by the power source; and a processor comprising hardware, the processor being configured to supply an adjusted voltage value from the power source to the imaging element based on a voltage value of the power-supply voltage detected in the imaging element and on the output voltage value detected by the voltage detector, calculate a delay time from timing when the voltage value of the power-supply voltage is detected in the imaging element until timing when the power source supplies the adjusted voltage value to the imaging element, and control supply timing when the power source supplies the adjusted voltage value based on the delay time.

15 Claims, 10 Drawing Sheets

(51) Int. Cl.
  *G02B 23/24*   (2006.01)
  *H02J 4/00*    (2006.01)
  *H04N 23/50*   (2023.01)
  *H04N 23/57*   (2023.01)
  *H04N 23/65*   (2023.01)
  *H04N 25/709*  (2023.01)

(52) U.S. Cl.
  CPC ............ *H04N 23/57* (2023.01); *H04N 23/65* (2023.01); *A61B 1/00011* (2013.01); *A61B 1/00112* (2013.01); *A61B 1/045* (2013.01); *G03B 2217/007* (2013.01); *H04N 23/555* (2023.01); *H04N 25/709* (2023.01)

(58) Field of Classification Search
  CPC ....... A61B 1/045; A61B 1/05; A61B 1/00011; A61B 1/00013; A61B 1/00016; A61B 1/00018; A61B 1/00029; A61B 1/00034; A61B 1/00036; A61B 1/00112; A61B 1/00114; A61B 1/00117; A61B 1/00119; A61B 1/00121; A61B 1/00124; A61B 1/00126; A61B 1/00128; H04N 23/52; H04N 23/57; H04N 23/60; H04N 23/65; H04N 23/651; H04N 25/709; H04N 23/555; G03B 2217/007; G02B 23/2484; H02J 4/00

See application file for complete search history.

(56) References Cited

FOREIGN PATENT DOCUMENTS

| | | |
|---|---|---|
| JP | 2011-193369 A | 9/2011 |
| JP | 2013-187782 A | 9/2013 |
| JP | 2015-192696 A | 11/2015 |
| WO | 2018/220940 A1 | 12/2018 |

* cited by examiner

CONTROL DEVICE, ENDOSCOPE, AND CONTROL METHOD

CROSS-REFERENCE TO RELATED APPLICATION

This application is a continuation of International Application No. PCT/JP2020/007780, filed on Feb. 26, 2020, the entire contents of which are incorporated herein by reference.

BACKGROUND

1. Technical Field

The present disclosure relates to a control device to which an endoscope that generates image data by capturing images within a subject is detachably connected, the endoscope, and a control method.

2. Related Art

In an endoscope, a technique is known for always driving an imaging element in an optimum state regardless of the individual difference in the imaging element or the individual difference in a cable by adjusting a power-supply voltage for driving the imaging element provided at a distal end of an insertion portion to be inserted into a subject to an appropriate value according to the imaging element (see, for example, Japanese Patent Application Laid-open No. 2010-88656). This technique drives the imaging element in the optimum state regardless of the individual difference in the imaging element by determining an adjustment value for adjusting the power-supply voltage to an appropriate value based on information on the endoscope connected to a control device and converting this determined adjustment value from a digital signal to an analog signal and outputting the signal to a power supply circuit.

SUMMARY

In some embodiments, a control device includes: a power source configured to supply a predetermined power-supply voltage to an imaging element; a voltage detector configured to detect an output voltage value of the power-supply voltage supplied by the power source; and a processor comprising hardware, the processor being configured to supply an adjusted voltage value from the power source to the imaging element based on a voltage value of the power-supply voltage detected in the imaging element and on the output voltage value detected by the voltage detector, calculate a delay time from timing when the voltage value of the power-supply voltage is detected in the imaging element until timing when the power source supplies the adjusted voltage value to the imaging element, and control supply timing when the power source supplies the adjusted voltage value based on the delay time.

In some embodiments, an endoscope includes: an imaging element provided at a distal end in an insertion portion of the endoscope configured to be inserted into a subject; a power generator configured to generate a predetermined power-supply voltage from a power-supply voltage input from an outside of the power generator to supply to the imaging element; a voltage detector configured to detect an output voltage value of the power-supply voltage supplied by the power generator; and a processor comprising hardware, the processor being configured to supply an adjusted voltage value from the power generator to the imaging element based on a voltage value of the power-supply voltage detected in the imaging element and on the output voltage value detected by the voltage detector, calculate a delay time from timing when the voltage value of the power-supply voltage is detected in the imaging element until timing when the power generator supplies the adjusted voltage value to the imaging element, and control supply timing when the power generator supplies the adjusted voltage value based on the delay time.

In some embodiments, provided is a control method executed by a control device including a power source configured to supply a predetermined power-supply voltage to an imaging element. The control method includes: detecting an output voltage value of the power-supply voltage supplied by the power source; supplying an adjusted voltage value from the power source to the imaging element based on a voltage value of the power-supply voltage detected in the imaging element and on the output voltage value; calculating a delay time from timing when the voltage value of the power-supply voltage is detected in the imaging element until timing when the power source supplies the adjusted voltage value to the imaging element; and controlling supply timing when the power source supplies the adjusted voltage value based on the delay time.

The above and other features, advantages and technical and industrial significance of this disclosure will be better understood by reading the following detailed description of presently preferred embodiments of the disclosure, when considered in connection with the accompanying drawings.

DETAILED DESCRIPTION

An endoscopic system including an imaging device will be described below as a mode for carrying out the present disclosure (hereinafter referred to as "embodiments"). However, the embodiments are not limited to this system, and can be applied to, for example, a vehicle-mounted camera including an imaging device, a surgical microscope, a machine vision camera, and a surveillance camera. The embodiments do not limit the disclosure. Furthermore, in the description of drawings, the same parts will be denoted with the same reference symbol. Furthermore, it should be noted that the drawings are schematic, and the relationship between the thickness and width of each member, the ratio of each member, and the like are different from actual members. Even between the drawings, parts having dimensions and ratios different from each other are included.

First Embodiment

Configuration of Endoscopic System

Figure 1:
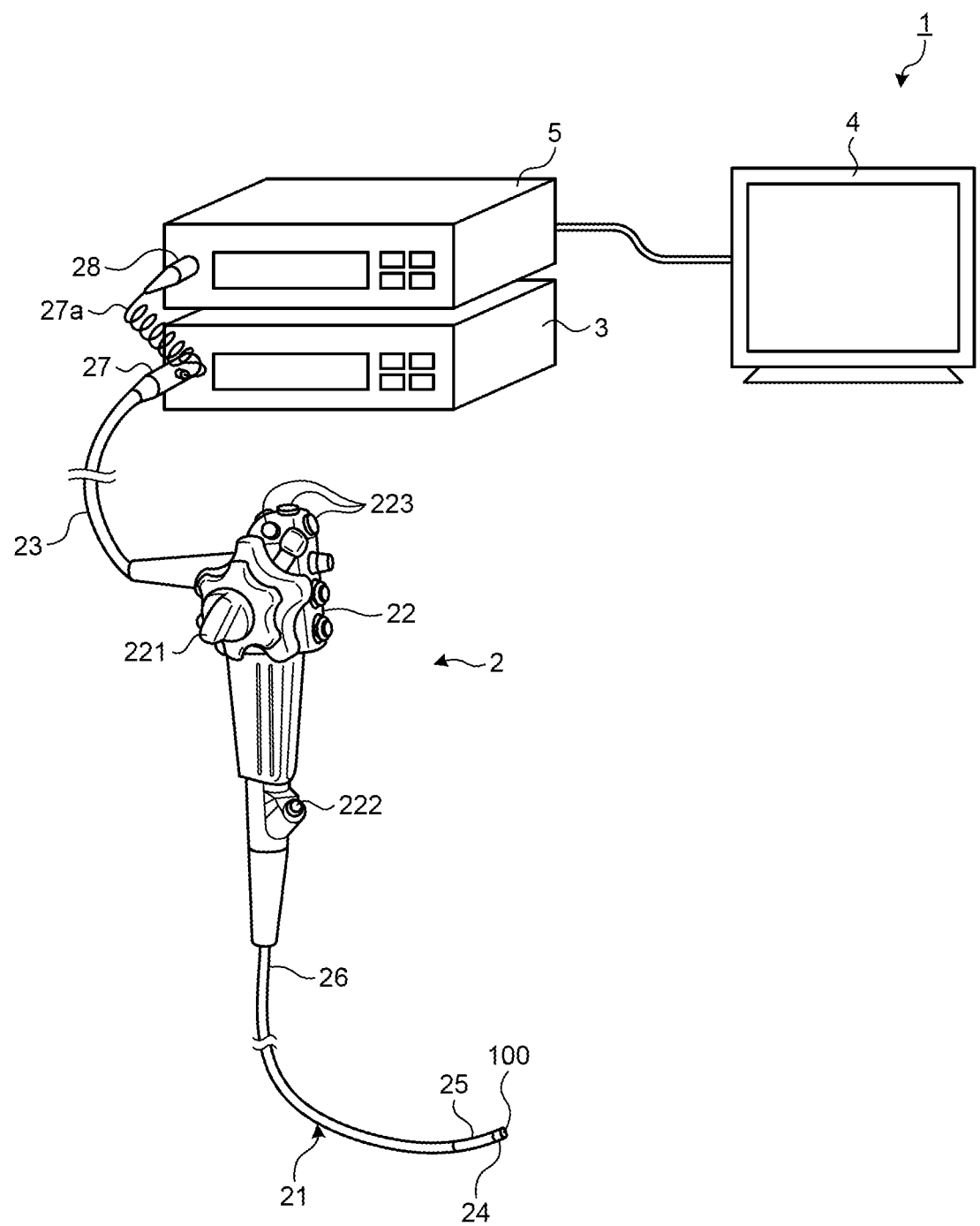
FIG. 1 is a diagram schematically illustrating an overall configuration of an endoscopic system according to a first embodiment.

FIG. 1 is a diagram schematically illustrating an overall configuration of an endoscopic system according to the first embodiment. The endoscopic system 1 illustrated in FIG. 1 captures an image inside a subject such as a patient by inserting an insertion portion of an endoscope into the subject and displays a display image on a display device based on a captured video signal. A user such as a doctor observes the display image displayed on the display device. The endoscopic system 1 includes an endoscope 2, a light source device 3, a display device 4, and a control device 5.
Configuration of Endoscope To begin with, the configuration of the endoscope 2 will be described.

The endoscope 2 generates a video signal obtained by capturing an image inside the subject (RAW data), and outputs the generated video signal to the control device 5. The endoscope 2 includes an insertion portion 21, an operating unit 22, and a universal cord 23.

The insertion portion 21 is inserted into the subject. The insertion portion 21 has an elongated shape having flexibility. The insertion portion 21 includes a distal end 24 including a built-in imaging device 100 described later, a bendable portion 25 that is bendable and includes a plurality of curve pieces, and a long flexible tube portion 26 connected to a proximal end side of the bendable portion 25 and having flexibility.

The distal end 24 includes glass fiber and the like. The distal end 24 includes a light guide (not illustrated) that forms a light guide path for illumination light supplied from the light source device 3, an illumination optical system provided at the tip of the light guide, and the imaging device 100 described later.

The operating unit 22 includes a curving knob 221 that curves the bendable portion 25 in an up-and-down direction and right-and-left direction, a treatment tool insertion portion 222 through which a treatment tool such as a biological forceps, a laser scalpel, and a test probe is inserted into the body cavity, and a plurality of switches 223 that is an operation input unit for inputting an operation instruction signal for a peripheral device such as air supply means, water supply means, and gas supply means in addition to the light source device 3 and the control device 5, and a pre-freeze signal instructing the imaging device 100 to capture a still image. The treatment tool inserted from the treatment tool insertion portion 222 appears from an aperture (not illustrated) via a treatment tool channel (not illustrated) of the distal end 24.

The universal cord 23 incorporates at least the light guide and an aggregated cable that brings together one or more cables. The aggregated cable includes a signal line for transmitting and receiving signals between the endoscope 2, the light source device 3, and the control device 5, the signal line transmitting and receiving captured images (image data), a signal line for transmitting and receiving drive timing signals for driving the imaging device 100 (synchronizing signal and clock signal), a signal line for supplying power to the imaging device 100, and the like. The universal cord 23 includes a connector unit 27, which is attachable and detachable to and from the light source device 3. A coil-shaped coil cable 27a extends from the connector unit 27. A connector unit 28 that is attachable and detachable to/from the control device 5 is provided at the extending end of the coil cable 27a.
Configuration of Light Source Device Next, the configuration of the light source device 3 will be described.

The light source device 3 supplies the illumination light with which the endoscope 2 irradiates the subject under the control of the control device 5. The light source device 3 is implemented using, for example, a halogen lamp, a laser diode (LD), a white light emitting diode (LED), or the like. The light source device 3 supplies the illumination light to the distal end 24 of the insertion portion 21 via the connector unit 27, the universal cord 23, and the insertion portion 21. Here, the illumination light is either one of white light or special light (for example, narrow band imaging (NBI) or infrared light).

Configuration of display device Next, the configuration of the display device 4 will be described.

The display device 4 displays the display image based on an imaging signal input from the control device 5 under the control of the control device 5. The display device 4 is implemented using a display panel such as an organic electro luminescence (EL) or a liquid crystal display.
Configuration of Control Device Next, the configuration of the control device 5 will be described.

Figure 2:
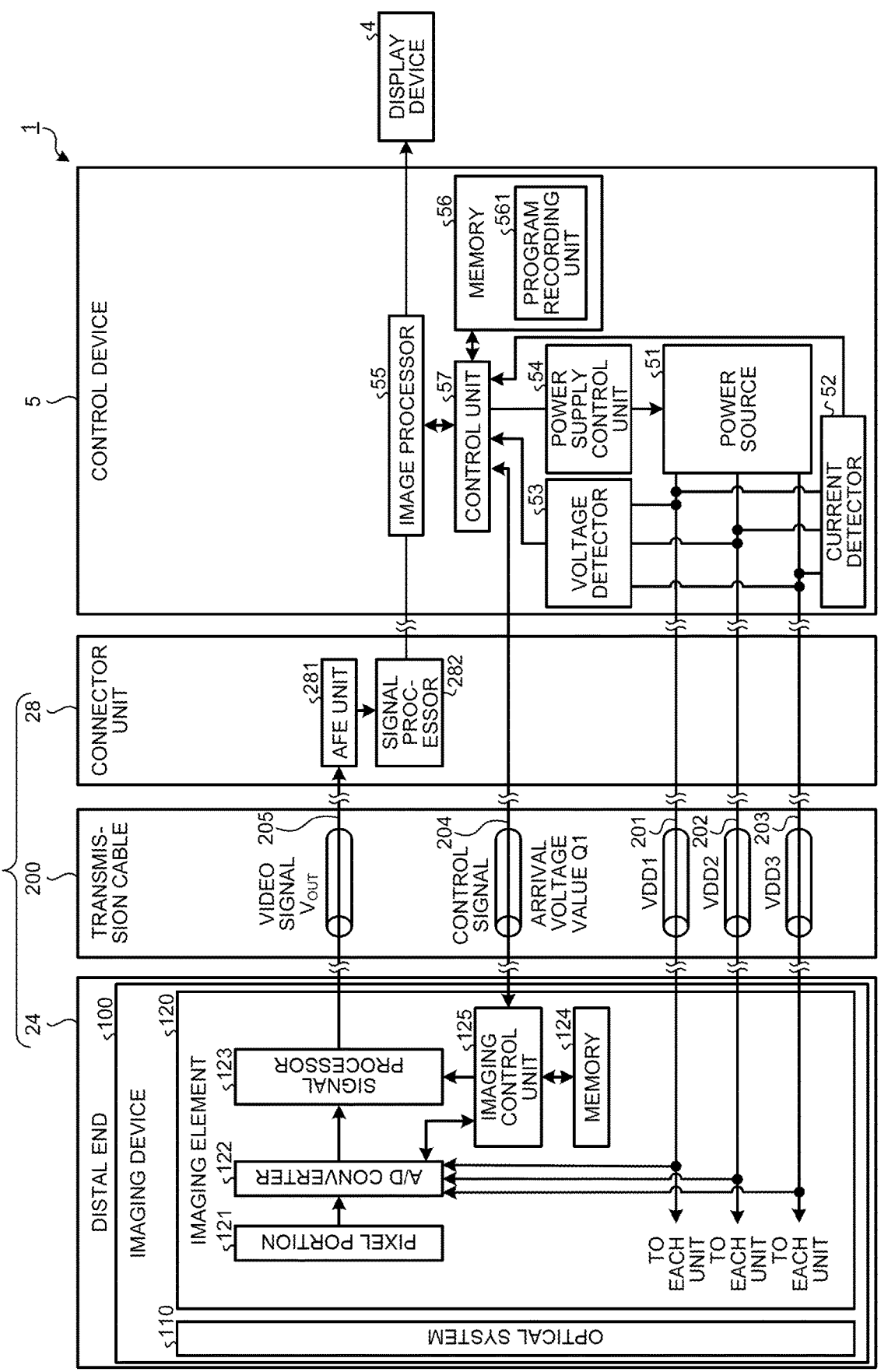
FIG. 2 is a block diagram illustrating a functional configuration of main units of an endoscope and a control device in the endoscopic system according to the first embodiment.

The control device 5 controls each unit of the endoscopic system 1. The control device 5 performs various types of image processing on the video signal input from the endoscope 2 and outputs the video signal to the display device 4. The control device 5 supplies the illumination light to the endoscope 2 by controlling the light source device 3.
Main Units of Endoscopic System Next, the configuration of main units of the endoscope 2 and the control device 5 described above will be described. FIG. 2 is a block diagram illustrating a functional configuration of main units of the endoscope 2 and the control device 5 in the endoscopic system 1.
Main Units of Endoscope To begin with, the functional configuration of main units of the endoscope will be described.

The endoscope 2 includes the imaging device 100, a transmission cable 200 built in the universal cord 23, and the connector unit 28.

To begin with, the imaging device 100 will be described.

The imaging device 100 is disposed at the distal end 24 of the endoscope 2, generates the video signal (RAW data) by capturing an image inside the subject, and outputs this video signal to the control device 5 via the transmission cable 200 of the universal cord 23 and the connector unit 28. The imaging device 100 includes an optical system 110 and an imaging element 120.

The optical system 110 forms a subject image on a light-receiving surface of the imaging element 120 by collecting reflected light of the illumination light reflected off the subject. The optical system 110 is implemented using one or more lenses or the like.

The imaging element 120 receives the subject image formed by the optical system 110, generates a pixel signal by performing photoelectric conversion, and performs analog-to-digital (A/D) conversion processing, signal processing, and the like on this pixel signal to generate the digital video signal (RAW data). Then, the imaging element 120 outputs the video signal to the connector unit 28 via the transmission cable 200. The imaging element 120 is implemented using an image sensor such as a complementary metal oxide semiconductor (CMOS) or charge coupled device (CCD). The imaging element 120 includes a pixel portion 121, an A/D converter 122, a signal processor 123, a memory 124, and an imaging control unit 125.

The pixel portion 121 includes a plurality of pixels arranged in a two-dimensional matrix. The pixel portion 121 is implemented using photoelectric conversion elements (photodiode) or the like. The pixel portion 121 outputs the pixel signal of each pixel to the A/D converter 122 under the control of the imaging control unit 125. The pixel portion 121 is driven according to the power-supply voltage input from the control device 5 via the transmission cable 200.

The A/D converter 122 performs A/D conversion processing on the pixel signal input from the pixel portion 121 and outputs the signal to the signal processor 123 under the control of the imaging control unit 125. Under the control of the imaging control unit 125, the A/D converter 122 performs A/D conversion on a voltage value of the power-supply voltage that reaches the imaging element 120 via the transmission cable 200, the voltage value of the power-supply voltage for transmission as being detected within the imaging element 120 to a control unit 57 of the control device 5 described later (hereafter simply referred to as "arrival voltage value Q1"). The A/D converter 122 then outputs a result of the A/D conversion to the signal processor 123. Specifically, under the control of the imaging control unit 125, in a current consumption fluctuation period between a blanking period and a pixel readout period of the imaging element 120, the A/D converter 122 outputs a result of the A/D conversion performed on the arrival voltage value Q1 to the signal processor 123. The A/D converter 122 is electrically connected to each of a signal line 201, a signal line 202, and a signal line 203 of the transmission cable 200 described later. The A/D converter 122 is implemented using an A/D conversion circuit or the like.

Under the control of the imaging control unit 125, the signal processor 123 performs various types of signal processing on the digital pixel signal input from the A/D converter 122 to generate the digital video signal, and outputs this video signal to the transmission cable 200. Here, various types of signal processing include noise reduction processing, amplification processing, and the like. Under the control of the imaging control unit 125, the signal processor 123 outputs the arrival voltage value Q1 input from the A/D converter 122 to the transmission cable 200. The signal processor 123 is implemented using a noise reduction circuit, an output amplification circuit, and the like.

The memory 124 is implemented using a read only memory (ROM), a random access memory (RAM), or the like, and records various pieces of information about the imaging element 120. The memory 124 records various programs executed by the imaging element 120, data being processed, identification information for identifying the imaging element 120, performance information on the imaging element 120 (drive voltage and drive current), defective pixel information on black and white defects in the pixel portion 121, and the like.

The imaging control unit 125 controls operations of respective units that constitute the imaging element 120 in response to a control signal input from the control device 5 via the transmission cable 200. Here, examples of the control signal include synchronizing signals (vertical synchronizing signal and horizontal synchronizing signal), a clock signal, a mode signal for instructing the operation of the imaging element 120, and the like. The imaging control unit 125 causes the pixel signal to be output from each pixel of a predetermined readout line in the pixel portion 121 to the A/D converter 122 in response to the control signal input from the control device 5 via the transmission cable 200. The imaging control unit 125 includes a timing generator (TG), a vertical scanning circuit, a horizontal scanning circuit, and the like.

Next, the transmission cable 200 will be described.

The transmission cable 200 is implemented using a plurality of signal lines. Specifically, the transmission cable 200 includes at least the signal line 201, the signal line 202, the signal line 203, a signal line 204, and a signal line 205. The signal line 201 transmits a power-supply voltage VDD1 input from the control device 5 to the imaging element 120. The signal line 202 transmits a power-supply voltage VDD2 input from the control device 5 to the imaging element 120. The signal line 203 transmits a power-supply voltage VDD3 input from the control device 5 to the imaging element 120. The signal line 204 transmits the control signal input from the control device 5 to the imaging element 120. The signal line 204 also transmits the arrival voltage values of the power-supply voltages VDD1 to VDD3 that are input from the imaging element 120 and have arrived at the imaging element 120 to the control device 5. The signal line 205 transmits the video signal $V_{out}$ input from the imaging element 120 to the connector unit 28.

Next, the connector unit 28 will be described.

The connector unit 28 is detachably connected to the control device 5. The connector unit 28 includes at least an analog front end unit 281 (hereinafter referred to as "AFE unit 281") and a signal processor 282.

The AFE unit 281 performs processing such as noise removal on the video signal $V_{out}$ transmitted from the signal line 205 and outputs the signal to the signal processor 282.

The signal processor 282 performs predetermined signal processing, for example, format conversion processing, gain-up processing, D/A conversion processing, and the like on the video signal $V_{out}$ input from the AFE unit 281, and outputs the signal to the control device 5.

Main Units of Control Device Next, main units of the control device 5 will be described.

The control device 5 includes a power source 51, a current detector 52, a voltage detector 53, a power supply control unit 54, an image processor 55, a memory 56, and the control unit 57.

Under the control of the power supply control unit 54, the power source 51 adjusts the power-supply voltage input from an external power supply to a plurality of power-supply voltages (power-supply voltage VDD1 to power-supply voltage VDD3) and outputs the power-supply voltages to the transmission cable 200 (signal line 201 to signal line 203).

The power source 51 is implemented using, for example, a smoothing circuit, a rectifier circuit, a transformer, or the like.

The current detector 52 is electrically connected to each of the signal line 201 to the signal line 203. The current detector 52 detects a current value of each of the signal line 201 to the signal line 203, and outputs this detection result to the control unit 57. The current detector 52 is implemented using an ammeter or the like.

The voltage detector 53 is electrically connected to each of the signal line 201 to the signal line 203. The voltage detector 53 detects a voltage value of each of the signal line 201 to the signal line 203, and outputs this detection result to the control unit 57. The voltage detector 53 is implemented using a voltmeter or the like.

Under the control of the control unit 57, the power supply control unit 54 adjusts the voltage values of the plurality of power-supply voltages output by the power source 51 to predetermined voltage values and causes the power source 51 to output the voltage values. The power supply control unit 54 is implemented using a memory and hardware such as a central processing unit (CPU).

The image processor 55 performs various types of image processing on the video signal input from the signal processor 282 of the connector unit 28 and outputs the signal to the display device 4. Here, the various types of image processing are demosaicing processing, white balance adjustment processing, γ correction processing, and the like. The image processor 55 is implemented using a memory and hardware such as a field programmable gate array (FPGA) or a graphics processing unit (GPU).

The memory 56 records various pieces of information about the control device 5, image data corresponding to the video signal, data being processed, and the like. Furthermore, the memory 56 includes a program recording unit 561 that records various programs executed by the control device 5. The memory 56 is implemented using a volatile memory, a non-volatile memory, and the like. Note that the memory 56 may be implemented using a memory card that can be mounted from the outside, or the like.

The control unit 57 controls each unit constituting the endoscopic system 1. The control unit 57 is implemented using a memory and hardware such as a central processing unit (CPU) or FPGA. The control unit 57 supplies the adjusted voltage value from the power source 51 to the imaging element 120 by controlling the power supply control unit 54 based on the arrival voltage value Q1 detected in the imaging element 120 and transmitted from the imaging element 120, and the output voltage value detected by the voltage detector 53. Furthermore, by controlling the power supply control unit 54, the control unit 57 calculates delay time (time lag) from timing when the imaging element 120 detects the arrival voltage value Q1 until timing when the power source 51 supplies the adjusted voltage value to the imaging element 120, and based on this delay time, the control unit 57 controls supply timing when the power source 51 supplies the adjusted voltage value. Specifically, after one frame period of the imaging element 120 of which the delay time is calculated elapses, or after one line elapses when the imaging element 120 reads the video signal (pixel signal), the control unit 57 causes the power source 51 to supply the adjusted voltage value to the imaging element 120 with delay of the delay time.

Processing of Control Device

Figure 3:
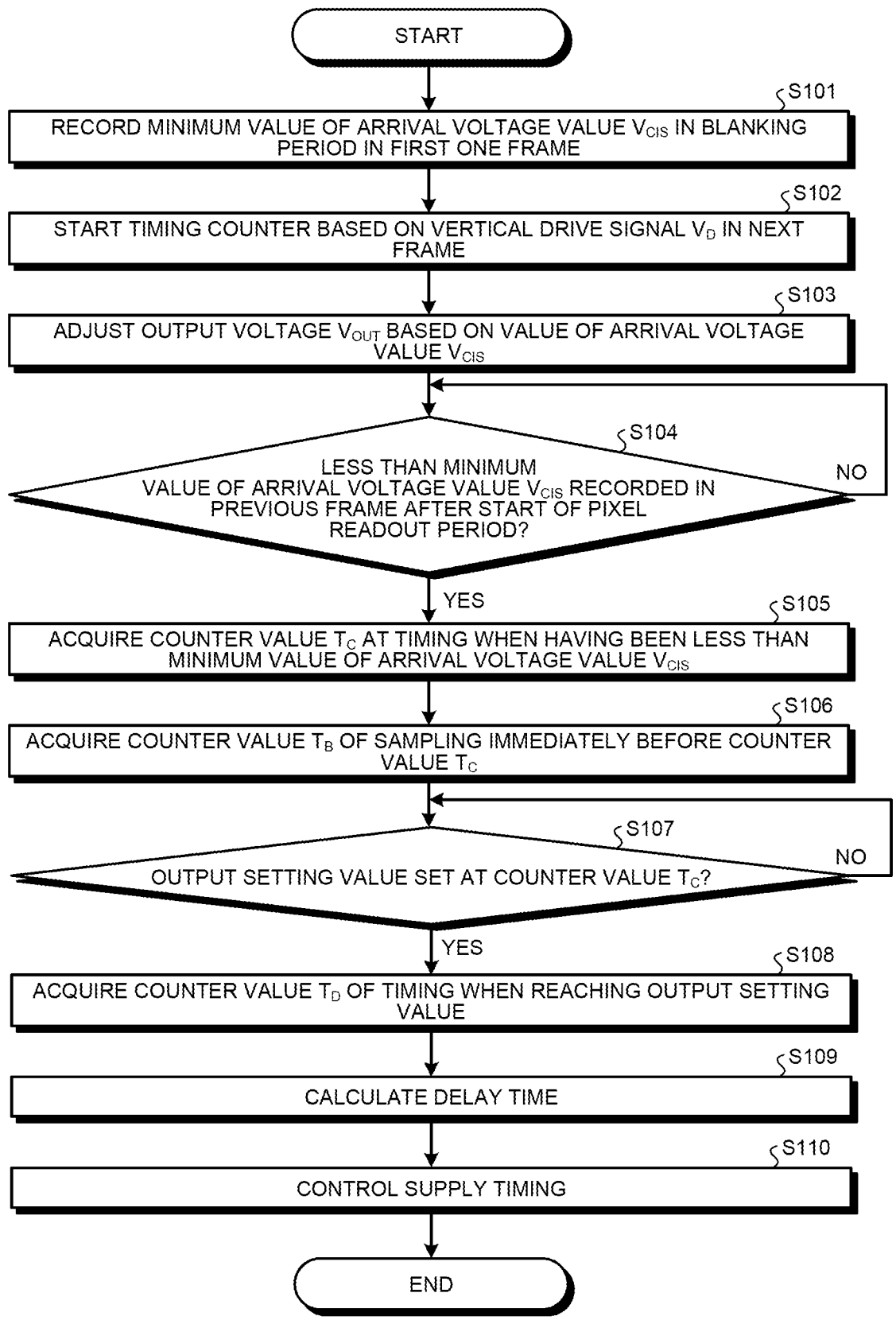
FIG. 3 is a flowchart illustrating an outline of processing performed by the control device according to the first embodiment.
Figure 4:
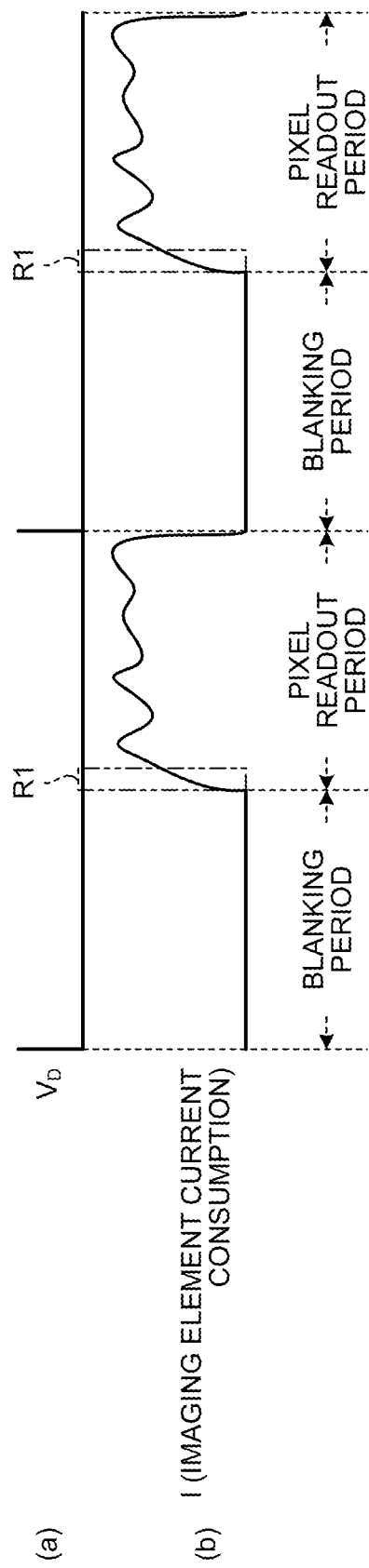
FIG. 4 is a diagram illustrating current consumption of an imaging element 120 and timing of a vertical drive signal during the processing performed by the control device according to the first embodiment.
Figure 5:
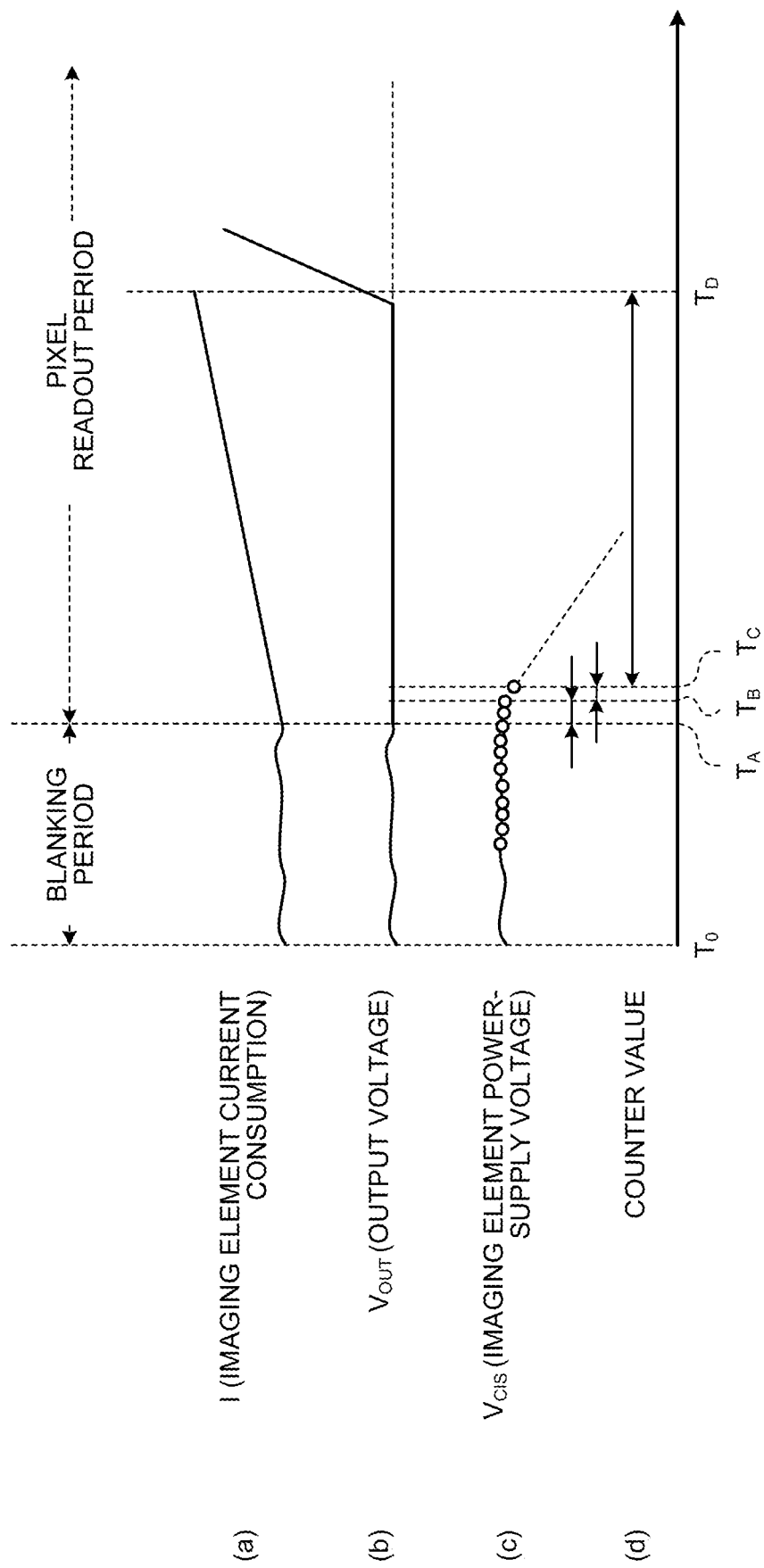
FIG. 5 is a diagram schematically illustrating a relationship between an expanded current consumption fluctuation period between a blanking period and a pixel readout period of the imaging element and each voltage in FIG. 4.

Next, the processing performed by the control device 5 will be described. FIG. 3 is a flowchart illustrating an outline of processing performed by the control device 5. FIG. 4 is a diagram illustrating current consumption of the imaging element 120 and timing of a vertical drive signal during the processing performed by the control device 5. FIG. 5 is a diagram schematically illustrating a relationship between an expanded current consumption fluctuation period R1 between the blanking period and the pixel readout period of the imaging element 120 and each voltage in FIG. 4. Note that in FIG. 4, from the upper row, (a) illustrates rising timing of a vertical drive signal $V_D$, and (b) illustrates current consumption I of the imaging element 120. Furthermore, in FIG. 5, from the upper row, (a) illustrates the current consumption I of the imaging element 120, (b) illustrates the output voltage of the video signal $V_{out}$ output from the imaging element 120, (c) illustrates the arrival voltage value $V_{CIS}$ that arrives at the imaging element 120, and (d) illustrates a counter value timed by the control unit 57.

As illustrated in FIG. 3, to begin with, after turning on the endoscopic system 1, the control unit 57 records, in the memory 56, the minimum value of the arrival voltage value $V_{CIS}$ of the power-supply voltage of the imaging element 120 in the blanking period in the first one frame of the imaging element 120 (step S101).

Subsequently, the control unit 57 starts timing the counter in the next frame of the imaging element 120 based on the vertical drive signal $V_D$ (step S102).

Thereafter, based on the voltage value of the arrival voltage value $V_{CIS}$ of the imaging element 120 acquired from the A/D converter 122 of the imaging element 120, the control unit 57 adjusts the output voltage $V_{OUT}$ of the imaging element 120 (step S103). In this case, as illustrated in FIG. 5, by controlling the power supply control unit 54, the control unit 57 adjusts the voltage value of the output voltage output by the power source 51 such that the output voltage $V_{OUT}$ of the imaging element 120 is a constant voltage value.

Subsequently, after the start of the pixel readout period of the imaging element 120 (see FIGS. 4 and 5), the control unit 57 determines whether the voltage value of the arrival voltage value $V_{CIS}$ acquired from the A/D converter 122 of the imaging element 120 is less than the minimum value of the arrival voltage value $V_{CIS}$ of the previous frame (first one frame) of the imaging element 120 recorded by the memory 56 (step S104). Specifically, the control unit 57 determines whether the voltage value of the arrival voltage value $V_{CIS}$ detected by the A/D converter 122 of the imaging element 120 is less than the minimum value of the arrival voltage value $V_{CIS}$ at the counter value $T_A$ recorded by the memory 56. When the control unit 57 determines that the voltage value of the arrival voltage value $V_{CIS}$ detected by the A/D converter 122 of the imaging element 120 is less than the minimum value of the arrival voltage value $V_{CIS}$ of the previous frame (first one frame) of the imaging element 120 recorded by the memory 56 (step S104: Yes), the control device 5 proceeds to step S105 described later. In contrast, when the control unit 57 determines that the voltage value of the arrival voltage value $V_{CIS}$ acquired by the A/D converter 122 of the imaging element 120 is not less than the minimum value of the arrival voltage value $V_{CIS}$ of the previous frame (first one frame) of the imaging element 120 recorded by the memory 56 (step S104: No), the control device 5 makes this determination at each predetermined timing (clock signal rising timing).

In step S105, the control unit 57 acquires the counter value $T_c$ at the timing when the voltage value of the arrival voltage value $V_{CIS}$ acquired by the A/D converter 122 of the imaging element 120 has been less than the minimum value of the arrival voltage value $V_{CIS}$ of the previous frame (first one frame) of the imaging element 120 recorded by the memory 56 (see FIG. 5).

Subsequently, the control unit 57 acquires the counter value $T_B$ (see FIG. 5) of the sampling point immediately before the counter value $T_C$ (step S106). Here, from the counter value $T_B$ to the counter value $T_C$ (counter value $T_B$—counter value $T_C$) is the time of one clock of the counter cycle by the control unit 57.

Thereafter, based on the detection result detected by the voltage detector 53, the control unit 57 determines whether the voltage value of the output voltage output by the power source 51 has reached the adjusted voltage value that is the output setting value set at the counter value $T_C$ (step S107). When the control unit 57 determines that the voltage value of the output voltage output by the power source 51 has reached the adjusted voltage value that is the output setting value set at the counter value $T_C$ (step S107: Yes), the control device 5 proceeds to step S108 described later. In contrast, when the control unit 57 determines that the voltage value of the output voltage output by the power source 51 has not reached the adjusted voltage value that is the output setting value set at the counter value $T_C$ (step S107: No), the control device 5 makes this determination at each predetermined timing (clock signal rising timing).

In step S108, the control unit 57 acquires the counter value $T_B$ of the timing when the voltage value of the output voltage output by the power source 51 reaches the adjusted voltage value that is the output setting value set at the counter value $T_C$ (see FIG. 5). Here, from the counter value $T_C$ to the counter value $T_D$ (counter value $T_C$—counter value $T_D$) is the time until the voltage value of the output voltage output by the power source 51 reaches the adjusted voltage value that is the output setting value set at the counter value $T_C$.

Subsequently, in the current consumption fluctuation period R1 between the blanking period and the pixel readout period of the imaging element 120, the control unit 57 calculates the delay time (time lag) from the timing when the arrival voltage value $V_{CIS}$ is detected in the imaging element 120 until the timing when the power source 51 supplies the adjusted voltage value obtained by adjusting the voltage value of the power-supply voltage according to the arrival voltage value $V_{CIS}$ detected in the imaging element 120 to the imaging element 120 (step S109). Specifically, the control unit 57 calculates the delay time by using the counter value $T_A$, the counter value $T_B$, the counter value $T_C$, and the counter value $T_D$ indicating the end timing of the blanking period in the current consumption fluctuation period R1. More specifically, when the delay time is $T_L$, the control unit 57 calculates the delay time $T_L$ by the following formula (1).

$$T_L = (T_D - T_C) + (T_B - T_A) \tag{1}$$

Thereafter, based on the delay time calculated in step S109 described above, the control unit 57 controls the supply timing when the power source 51 supplies the adjusted voltage value to the imaging element 120 (step S110). After step S110, the control device 5 ends this processing.

Figure 6:
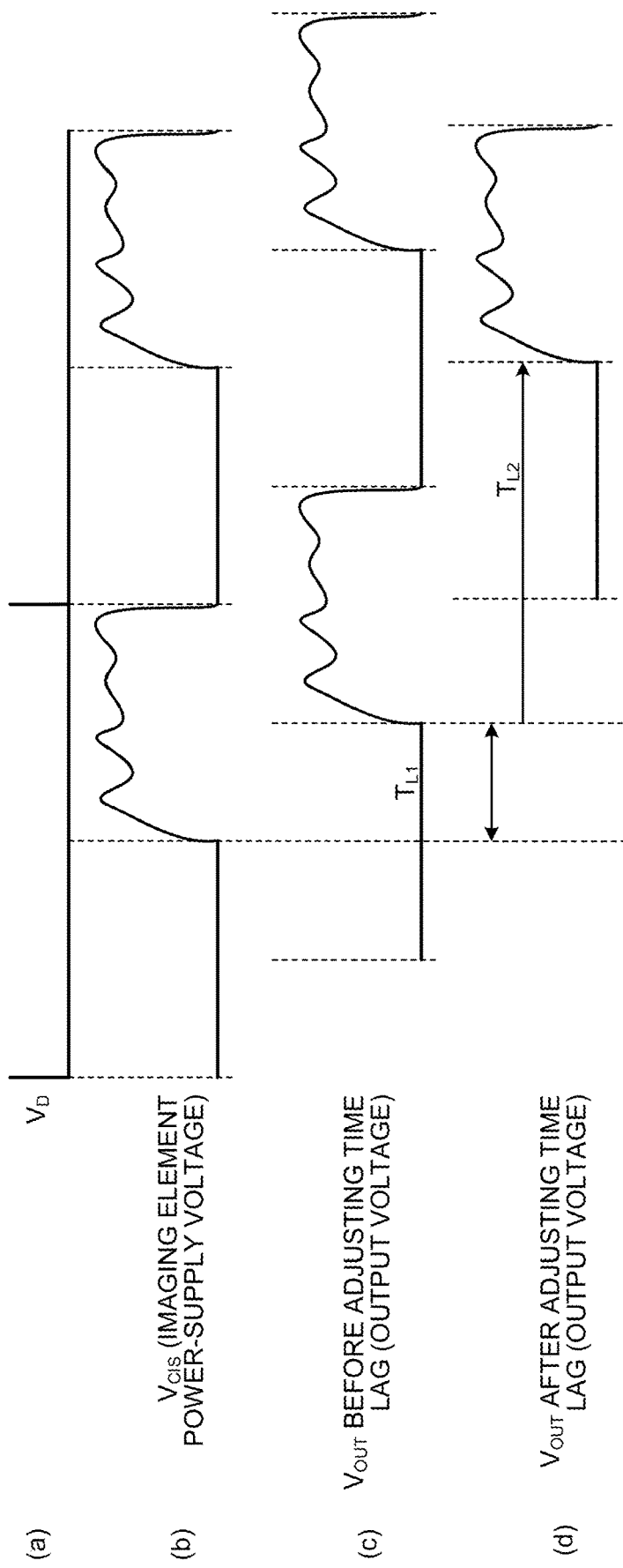
FIG. 6 is a diagram schematically illustrating supply timing of a power source controlled by a control unit according to the first embodiment.

FIG. 6 is a diagram schematically illustrating supply timing of the power source 51 controlled by the control unit 57. In FIG. 6, (a) illustrates the rising timing of the vertical drive signal, (b) illustrates the power-supply voltage of the imaging element 120, (c) illustrates the output voltage of the power source 51 before adjusting the delay time, and (d) illustrates the output voltage of the power source 51 after adjusting the delay time.

As illustrated in (c) of FIG. 6, with the conventional technique, when the control unit 57 causes the power source 51 to output the adjusted voltage value, by controlling the power supply control unit 54 based on the arrival voltage value detected by the A/D converter 122 of the imaging element 120, a delay time $T_{L1}$ occurs. Therefore, with the conventional technique, the voltage value of the power-supply voltage supplied to the imaging element 120 of the endoscope 2 is set by taking into account the change in the current consumption value that occurs in the blanking period and the pixel charge readout period of the imaging element 120, individual difference of the imaging element 120 and individual difference of the transmission cable 200 (resistance value), and the like, and an adjustment is made in advance to a higher range including the recommended operating range of the imaging element 120. Accordingly, with the conventional technique, the power-supply voltage that reaches the imaging element 120 of the endoscope 2 from the control device 5 via the transmission cable 200 has a higher value. As a result, with the conventional technique, it is necessary to select a signal line that can transmit a high power-supply voltage, and therefore the signal line of the transmission cable 200 (for example, the signal line 205 transmitting the video signal $V_{out}$) cannot be reduced in diameter.

In contrast, as illustrated in (d) of FIG. 6, the control unit 57 controls the supply timing when the power source 51 supplies the adjusted voltage value to the imaging element 120 based on the delay time. Specifically, by shifting the timing of causing the power source 51 to output the adjusted voltage value to the next frame of the imaging element 120 by a delay time $T_{L2}$, the control unit 57 matches the timing of causing the power source 51 to output the adjusted voltage value to the fluctuation timing when the voltage of the imaging element 120 fluctuates. This allows the adjustment timing of the power-supply voltage to be appropriately performed. Furthermore, the control unit 57 controls the supply timing when the power source 51 supplies the adjusted voltage value to the imaging element 120 based on the delay time, therefore the signal line 205 of the transmission cable 200 can be reduced in diameter.

According to the first embodiment described above, the control unit 57 calculates the delay time from the timing of the arrival voltage value Q1 detected in the imaging element 120 until the timing when the power source 51 supplies the adjusted voltage value to the imaging element 120, and controls the supply timing when the power source 51 supplies the adjusted voltage value based on the delay time, thereby making it possible to match the timing of causing the power source 51 to output the adjusted voltage value with the fluctuation timing when the voltage of the imaging element 120 fluctuates, and therefore the adjustment timing of the power-supply voltage can be performed appropriately.

According to the first embodiment, since the control unit 57 causes the power source 51 to supply the adjusted voltage value with delay of the delay time after one frame period of the imaging element 120 of which the delay time is calculated elapses, it is possible to prevent timing shift of adjustment of the power-supply voltage and to perform an operation at the appropriate power-supply voltage.

According to the first embodiment, since the control unit 57 calculates the delay time in the current consumption fluctuation period between the blanking period and the pixel readout period of the imaging element 120, appropriate timing of the power-supply voltage can be calculated.

According to the first embodiment, since the A/D converter 122 of the imaging element 120 detects the arrival voltage value Q1, it is not necessary to separately provide a signal line for transmitting a control signal for a detection circuit for detecting the arrival voltage value Q1, and therefore the transmission cable 200 can be reduced in diameter.

Note that according to the first embodiment, after one frame period of the imaging element 120 of which the delay time is calculated elapses, the control unit 57 causes the power source 51 to supply the adjusted voltage value with delay of the delay time, but this is not restrictive. For example, after one line when the imaging element 120 reads the video signal elapses, the control unit 57 may cause the power source 51 to supply the adjusted voltage value with delay of the delay time.

Second Embodiment

Next, the second embodiment will be described. In the first embodiment described above, the arrival voltage value detected by the A/D converter 122 is transmitted to the control device 5 via the signal line 204 of the transmission cable 200. In the second embodiment, the arrival voltage value is transmitted to a control device 5 via a signal line 205 of a transmission cable 200 for transmitting a video signal $V_{out}$. In the following, the same components as those of the endoscopic system 1 according to the first embodiment described above are denoted with the same reference symbol, and detailed description thereof will be omitted.

Main Units of Endoscopic System

Figure 7:
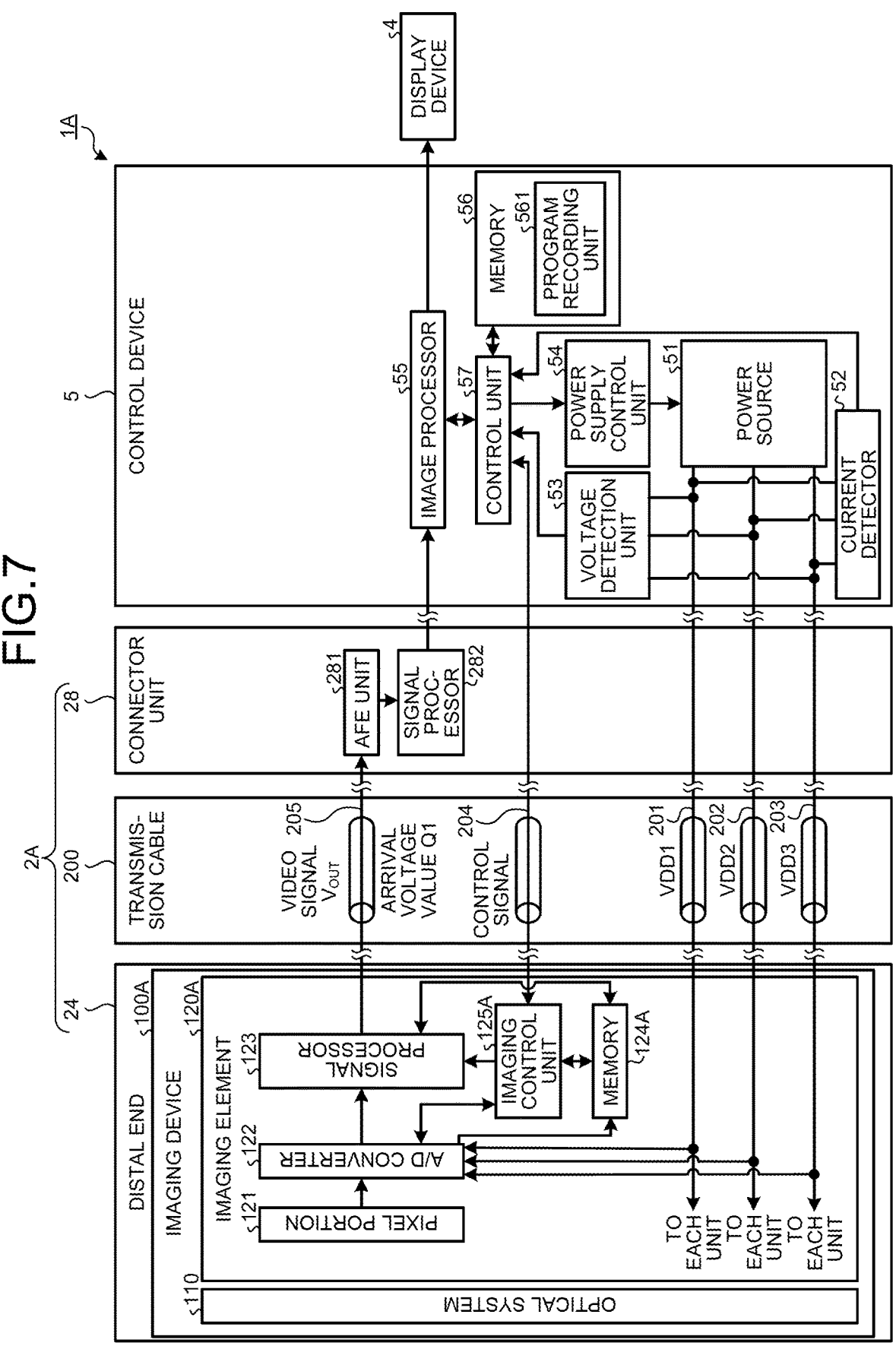
FIG. 7 is a block diagram illustrating a functional configuration of main units of an endoscope and a control device in an endoscopic system according to a second embodiment.

FIG. 7 is a block diagram illustrating a functional configuration of main units of an endoscope and a control device in an endoscopic system according to the second embodiment. The endoscopic system 1A illustrated in FIG. 7 includes an endoscope 2A in place of the endoscope 2 according to the first embodiment described above.

Main Units of Endoscope

The endoscope 2A illustrated in FIG. 7 includes an imaging device 100A in place of the imaging device 100 according to the first embodiment described above. The imaging device 100A includes an imaging element 120A in place of the imaging element 120 according to the first embodiment described above. Furthermore, the imaging element 120A includes a memory 124A and an imaging control unit 125A in place of the memory 124 and the imaging control unit 125 according to the first embodiment described above.

The memory 124A is electrically connected to each of an A/D converter 122 and a signal processor 123. The memory 124A records an arrival voltage value one frame before of the imaging element 120A detected by the A/D converter 122 under the control of the imaging control unit 125A. The memory 124A is implemented using a volatile memory, a non-volatile memory, and the like.

The imaging control unit 125A outputs, to the signal processor 123, the arrival voltage value Q1 one frame before of the imaging element 120A detected by the A/D converter 122 and recorded by the memory 124A in blanking period of the next frame of the imaging element 120A via the signal line 205 of the transmission cable 200. The imaging control unit 125A includes a timing generator (TG), a vertical scanning circuit, a horizontal scanning circuit, and the like.

Processing of Control Device

Figure 8:
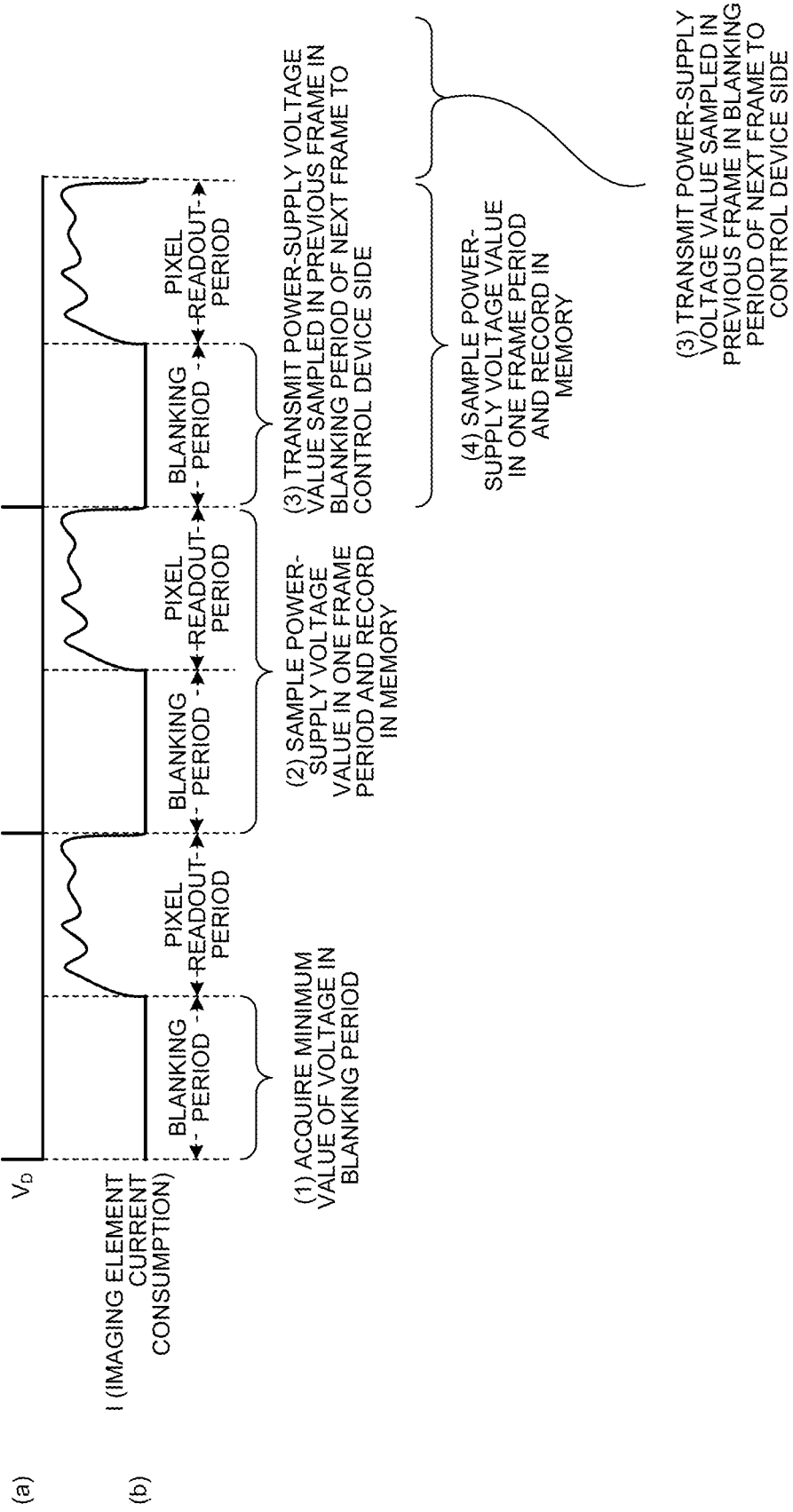
FIG. 8 is a timing chart schematically illustrating timing of an arrival voltage value acquired from an imaging element by the control device according to the second embodiment.

Next, timing of the arrival voltage value acquired from the imaging element 120A by the control device 5 will be described. FIG. 8 is a timing chart schematically illustrating timing of the arrival voltage value acquired from the imaging element 120A by the control device 5. In FIG. 8, from the upper row, (a) illustrates rising timing of a vertical drive signal, and (b) illustrates current consumption of the imaging element 120A.

As illustrated in FIG. 8, to begin with, the imaging control unit 125A acquires the minimum value of the arrival voltage value detected by the A/D converter 122 in the blanking period of the imaging element 120A and records the minimum value in the memory 124A.

Subsequently, as illustrated in FIG. 8, the imaging control unit 125A samples the arrival voltage value of one frame period of the imaging element 120A detected by the A/D converter 122 in response to a clock signal, and records this sampling result in the memory 124A.

Thereafter, as illustrated in FIG. 8, the imaging control unit 125A causes the signal processor 123 to output the arrival voltage value of the previous frame recorded by the memory 124A in the blanking period of the next frame in the imaging element 120A. In this case, the imaging control unit 125A samples the arrival voltage value of the next frame period of the imaging element 120A detected by the A/D converter 122 in response to a clock signal, and records this sampling result in the memory 124A.

In this way, the imaging control unit 125A causes the signal processor 123 to output the arrival voltage value Q1 of the previous frame recorded by the memory 124A in the blanking period of the imaging element 120A. In this case, since the signal processor 123 outputs the arrival voltage value Q1 to the control device 5 via the same signal line 205 for transmitting the video signal $V_{out}$, the signal line 204 can be reduced in diameter more than in the first embodiment described above.

According to the second embodiment described above, by controlling the supply timing when a power source 51 supplies the adjusted voltage value based on a delay time calculated by a control unit 57, it is possible to match the timing of causing the power source 51 to output the adjusted voltage value with fluctuation timing when the voltage of the imaging element 120A fluctuates, and therefore the adjustment timing of the power-supply voltage can be performed appropriately.

According to the second embodiment, since the imaging control unit 125A causes the signal processor 123 to output the arrival voltage value of the previous frame recorded by the memory 124A in the blanking period of the next frame in the imaging element 120A, it is not necessary to make the signal line 204 of the transmission cable 200 thick enough to enable a transmission at high bandwidth, and therefore the signal line 204 can be reduced in diameter.

Third Embodiment

Next, the third embodiment will be described. In the first embodiment described above, the A/D converter 122 is provided in the imaging element 120 to transmit digital data to the control device 5. In the third embodiment, analog data is transmitted to a control device 5B. In the following, the same components as those of the endoscopic system 1 according to the first embodiment described above are denoted with the same reference symbol, and detailed description thereof will be omitted.

Main Units of Endoscopic System

Figure 9:
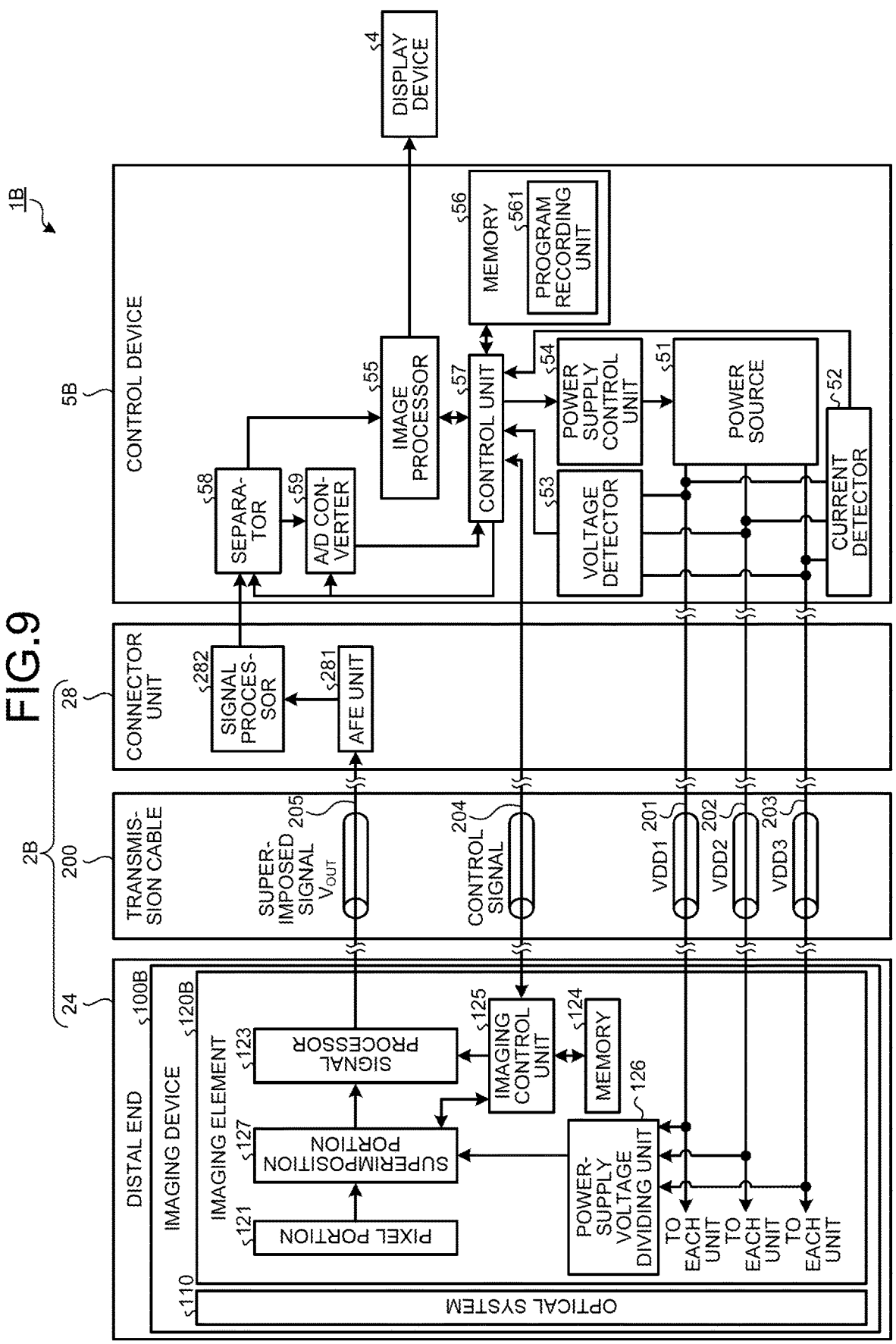
FIG. 9 is a block diagram illustrating a functional configuration of main units of an endoscope and a control device according to a third embodiment.

FIG. 9 is a block diagram illustrating a functional configuration of main units of an endoscope and a control device according to the third embodiment. An endoscopic system 1B illustrated in FIG. 9 includes an endoscope 2B and a control device 5B in place of the endoscope 2 and the control device 5 according to the first embodiment described above.

Main Units of Endoscope

To begin with, main units of the endoscope 2B will be described.

The endoscope 2B includes an imaging device 100B in place of the imaging device 100 according to the first embodiment described above. The imaging device 100B includes an imaging element 120B in place of the imaging element 120 according to the first embodiment described above. The imaging element 120B includes a power-supply voltage dividing unit 126 and a superimposition portion 127 in place of the A/D converter 122 according to the first embodiment described above.

The power-supply voltage dividing unit 126 outputs, to the superimposition portion 127, an arrival voltage value indicating a result of dividing a power-supply voltage VDD1, a power-supply voltage VDD2, and a power-supply voltage VDD3 from each of a signal line 201, a signal line 202, and a signal line 203 of a transmission cable 200. The power-supply voltage dividing unit 126 is implemented using a voltage dividing circuit or the like.

The superimposition portion 127 outputs, to a signal processor 123, a superimposed signal obtained by superimposing the arrival voltage value Q1 input from the power-supply voltage dividing unit 126 on a video signal $V_{out}$ input from a pixel portion 121, under the control of an imaging control unit 125. For example, the superimposition portion 127 converts the arrival voltage value Q1 input from the power-supply voltage dividing unit 126 into a negative voltage or an AC component, and superimposes this negative voltage or AC component on the video signal $V_{out}$ input from the pixel portion 121. The superimposition portion 127 is implemented using an amplifier, a capacitor that superimposes the arrival voltage value Q1 on the video signal $V_{out}$ input from the pixel portion 121, and the like.

Main Units of Control Device

Next, main units of the control device 5B will be described.

The control device 5B includes a separator 58 and an A/D converter 59 in addition to the configuration of the control device 5 according to the first embodiment described above.

Under the control of a control unit 57, the separator 58 separates the video signal $V_{out}$ and the arrival voltage value Q1 from the superimposed signal input via the signal line 205, the AFE unit 281, and the signal processor 282, and outputs the video signal $V_{out}$ to an image processor 55 and outputs the arrival voltage value Q1 to the A/D converter 59. The separator 58 is implemented using an amplifier, an RC circuit formed using a capacitor and a resistor (high-pass filter), and the like.

Under the control of the control unit 57, the A/D converter 59 generates the digital arrival voltage value Q1 by performing A/D conversion processing on the analog arrival voltage value Q1 input from the separator 58, and outputs the digital arrival voltage value Q1 to the control unit 57.

The third embodiment described above allows the adjustment timing of the power-supply voltage to be appropriately performed.

Note that in the third embodiment, the separator 58 and the A/D converter 59 are provided in the control device 5B, but this is not restrictive. The separator 58 and the A/D converter 59 may be provided, for example, in a connector unit 28 or an operating unit 22 of the endoscope 2B.

Fourth Embodiment

Next, the fourth embodiment will be described. In the first embodiment described above, the power source 51 of the control device 5 makes an adjustment to a plurality of power-supply voltages for output to the endoscope 2. In the fourth embodiment, an endoscope provides a power generator to generate a plurality of power-supply voltages in a connector unit, and outputs the plurality of power-supply voltages to an imaging device 100 of a distal end 24. In the following, the same components as those of the endoscopic system 1 according to the first embodiment described above are denoted with the same reference symbol, and detailed description thereof will be omitted.

Main Units of Endoscopic System

Figure 10:
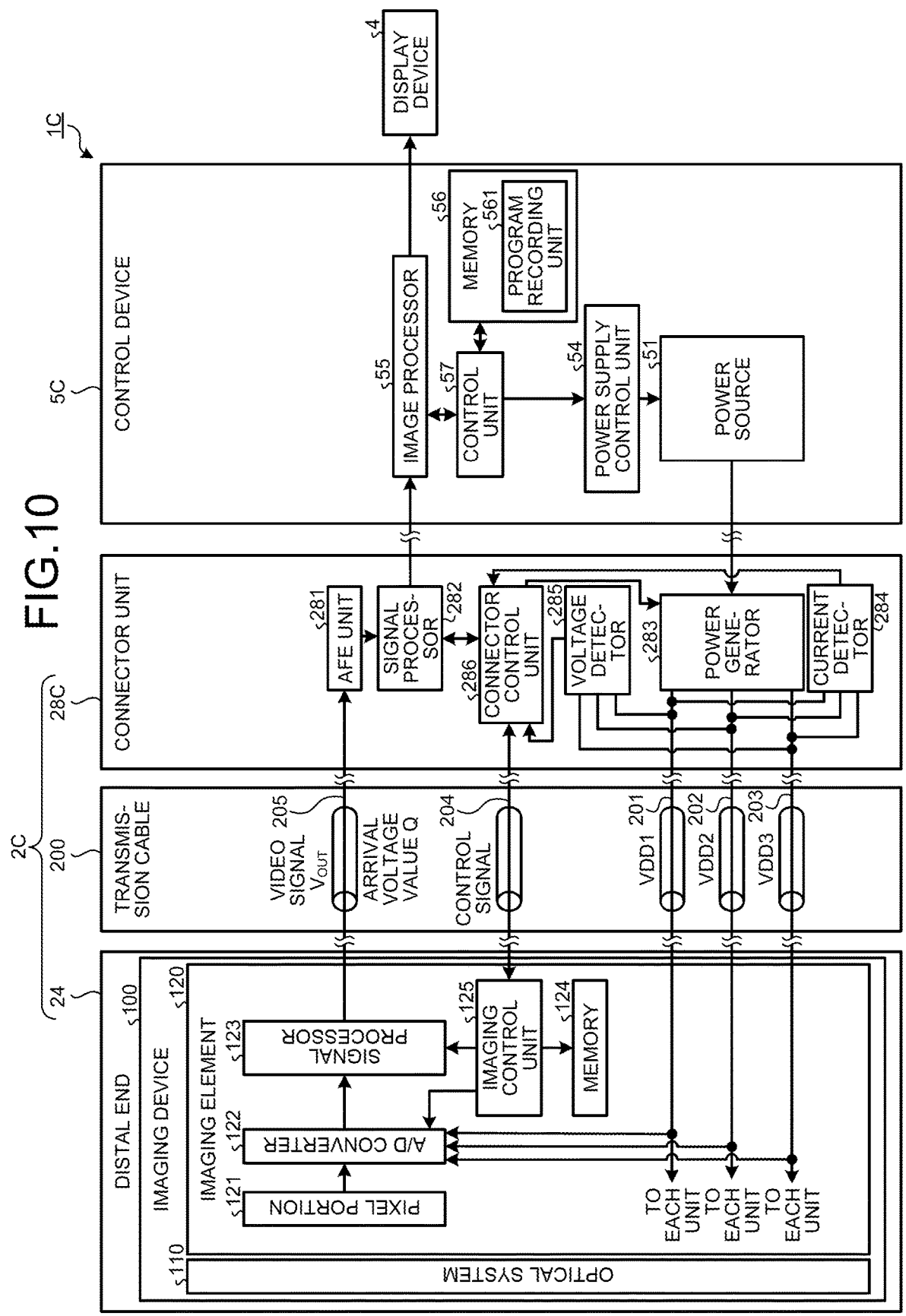
FIG. 10 is a block diagram illustrating a functional configuration of main units of an endoscope and a control device in an endoscopic system according to a fourth embodiment.

FIG. 10 is a block diagram illustrating a functional configuration of main units of an endoscope and a control device in an endoscopic system according to the fourth embodiment. An endoscopic system 1C illustrated in FIG. 10 includes an endoscope 2C and a control device 5C in place of the endoscope 2 and the control device 5 according to the first embodiment described above.

Main Units of Endoscope

To begin with, the configuration of main units of the endoscope 2C will be described.

The endoscope 2C includes a connector unit 28C in place of the connector unit 28 according to the first embodiment described above. The connector unit 28C includes a power generator 283, a current detector 284, a voltage detector 285, and a connector control unit 286, in addition to the configuration of the connector unit 28 according to the first embodiment described above.

Under the control of the connector control unit 286, the power generator 283 generates the power-supply voltage input from the power source 51 of the control device 5C into a plurality of power-supply voltages (power-supply voltage VDD1 to power-supply voltage VDD3) to output to a transmission cable 200 (signal line 201 to signal line 203). The power generator 283 is implemented using, for example, a smoothing circuit, a rectifier circuit, a transformer, or the like.

The current detector 284 is electrically connected to each of the signal line 201 to the signal line 203. The current detector 284 detects a current value of each of the signal line 201 to the signal line 203, and outputs this detection result to the connector control unit 286. The current detector 284 is implemented using an ammeter or the like.

The voltage detector 285 is electrically connected to each of the signal line 201 to the signal line 203. The voltage detector 285 detects a voltage value of each of the signal line 201 to the signal line 203, and outputs this detection result to the connector control unit 286. The voltage detector 285 is implemented using a voltmeter or the like.

The connector control unit 286 adjusts the voltage values of the plurality of power-supply voltages output by the power generator 283 to predetermined voltage values and causes the power generator 283 to output the voltages. The connector control unit 286 is implemented using a memory and hardware such as an FPGA.

Main Units of Control Device

Next, the configuration of the control device 5C will be described.

In the control device 5C, the current detector 52 and the voltage detector 53 are omitted from the configuration of the control device 5 according to the first embodiment described above.

The fourth embodiment described above allows the adjustment timing of the power-supply voltage to be appropriately performed.

Note that in the fourth embodiment described above, the connector unit 28C is provided with the power generator 283, the current detector 284, the voltage detector 285, and the connector control unit 286, but this is not restrictive, and these units may be provided, for example, in an operating unit 22.

Other Embodiments

Various embodiments can be formed by appropriately combining a plurality of components disclosed in the endoscopic system according to the first to fourth embodiments of the present disclosure described above. For example, some components may be deleted from all the components described in the endoscopic system according to the embodiments of the present disclosure described above. Furthermore, the components described in the endoscopic system according to the embodiments of the present disclosure described above may be appropriately combined.

In the endoscopic system according to the first to fourth embodiments of the present disclosure, the above-described "unit" can be read as "means" or "circuit". For example, the control unit can be read as a control means or a control circuit.

Note that in the description of the flowchart in the present specification, the context of processing between steps is clarified by using expressions such as "to begin with", "thereafter", and "subsequently". However, the order of processing required to carry out the disclosure is not uniquely determined by those expressions. That is, the order of processing in the flowchart described in the present specification can be changed within a consistent range.

Some embodiments of the present application have been described in detail above with reference to the drawings, but these are examples. Including aspects described in the present disclosure, it is possible to carry out the disclosure in other forms with various modifications and improvements based on the knowledge of those skilled in the art.

The present disclosure has an effect of preventing timing shift of voltage adjustment of the power-supply voltage supplied to the imaging element and operating at an appropriate power-supply voltage.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A control device comprising:
a power source configured to supply a predetermined power-supply voltage to an imaging element;
a voltage detector configured to detect an output voltage value of the power-supply voltage supplied by the power source; and
a processor comprising hardware, the processor being configured to
supply an adjusted voltage value from the power source to the imaging element based on a voltage value of the power-supply voltage detected in the imaging element and on the output voltage value detected by the voltage detector,
calculate a delay time from timing when the voltage value of the power-supply voltage is detected in the imaging element until timing when the power source supplies the adjusted voltage value to the imaging element, and control supply timing when the power source supplies the adjusted voltage value based on the delay time.

2. The control device according to claim 1, wherein the processor is configured to
cause the power source to supply the adjusted voltage value with delay of the delay time after one frame period of the imaging element of which the delay time is calculated elapses or after one line when the imaging element reads a video signal elapses.

3. The control device according to claim 1, wherein the processor is configured to
calculate the delay time in a current consumption fluctuation period between a blanking period and a pixel readout period of the imaging element.

4. The control device according to claim 1, wherein the processor is configured to:
record the voltage value in a blanking period in a first frame of the imaging element immediately after turning on the control device;
adjust the adjusted voltage value to be supplied by the power source to the imaging element based on the voltage value of the power-supply voltage detected in the imaging element and on the output voltage value detected by the voltage detector;
determine whether the voltage value detected in the imaging element is less than the voltage value recorded one frame before in the imaging element after the pixel readout period of the imaging element starts; and
calculate the delay time based on first timing when becoming less than the voltage value, sampling timing immediately before the first timing, detection timing when the voltage detector detects that the adjusted voltage value supplied by the power source becomes a value corresponding to the voltage value at the first timing, and end timing of the blanking period of the imaging element.

5. The control device according to claim 4, wherein the imaging element includes:
a pixel portion configured to generate a video signal according to an amount of received light; and
an analog-to-digital (A/D) converter configured to perform A/D conversion processing on the video signal to enable output to the control device, the A/D converter being configured to detect the voltage value of the power-supply voltage, and
the processor is configured to acquire the voltage value of the power-supply voltage detected by the A/D converter.

6. The control device according to claim 4, wherein the imaging element includes:
a pixel portion configured to generate a video signal according to an amount of received light;
an analog-to-digital (A/D) converter configured to perform A/D conversion processing on the video signal to enable output to the control device and to enable detection of the voltage value of the power-supply voltage; and
a memory configured to record a detection result in which the A/D converter detects the voltage value of the power-supply voltage, and
the processor is configured to acquire the detection result recorded by the memory in the blanking period of the imaging element as the voltage value of the power-supply voltage.

7. The control device according to claim 4, wherein the imaging element includes:

a pixel portion configured to generate a video signal according to an amount of received light; and
a superimposition portion configured to output a superimposed signal obtained by superimposing the voltage value of the power-supply voltage supplied from the power source on the video signal, and
the control device further includes a separator configured to separate the voltage value of the power-supply voltage from the superimposed signal to output to the processor.

8. An endoscope comprising:
an imaging element provided at a distal end in an insertion portion of the endoscope configured to be inserted into a subject;
a power generator configured to generate a predetermined power-supply voltage from a power-supply voltage input from an outside of the power generator to supply to the imaging element;
a voltage detector configured to detect an output voltage value of the power-supply voltage supplied by the power generator; and
a processor comprising hardware, the processor being configured to
supply an adjusted voltage value from the power generator to the imaging element based on a voltage value of the power-supply voltage detected in the imaging element and on the output voltage value detected by the voltage detector,
calculate a delay time from timing when the voltage value of the power-supply voltage is detected in the imaging element until timing when the power generator supplies the adjusted voltage value to the imaging element, and
control supply timing when the power generator supplies the adjusted voltage value based on the delay time.

9. A control method executed by a control device including a power source configured to supply a predetermined power-supply voltage to an imaging element, the control method comprising:
detecting an output voltage value of the power-supply voltage supplied by the power source;
supplying an adjusted voltage value from the power source to the imaging element based on a voltage value of the power-supply voltage detected in the imaging element and on the output voltage value;
calculating a delay time from timing when the voltage value of the power-supply voltage is detected in the imaging element until timing when the power source supplies the adjusted voltage value to the imaging element; and
controlling supply timing when the power source supplies the adjusted voltage value based on the delay time.

10. The control method according to claim 9, further comprising:
causing the power source to supply the adjusted voltage value with delay of the delay time after one frame period of the imaging element of which the delay time is calculated elapses or after one line when the imaging element reads a video signal elapses.

11. The control method according to claim 9, further comprising:
calculating the delay time in a current consumption fluctuation period between a blanking period and a pixel readout period of the imaging element.

12. The control method according to claim 9, further comprising:
recording the voltage value in a blanking period in a first frame of the imaging element immediately after turning on the control device;
adjusting the adjusted voltage value to be supplied by the power source to the imaging element based on the voltage value of the power-supply voltage detected in the imaging element and on the output voltage value;
determining whether the voltage value detected in the imaging element is less than the voltage value recorded one frame before in the imaging element after the pixel readout period of the imaging element starts; and
calculating the delay time based on first timing when becoming less than the voltage value, sampling timing immediately before the first timing, detection timing when detected that the adjusted voltage value supplied by the power source becomes a value corresponding to the voltage value at the first timing, and end timing of the blanking period of the imaging element.

13. The control method according to claim 12,
wherein the imaging element includes:
a pixel portion configured to generate a video signal according to an amount of received light; and
an analog-to-digital (A/D) converter configured to perform A/D conversion processing on the video signal to enable output to the control device,
the A/D converter configured to detect the voltage value of the power-supply voltage, and
the control method further comprising
acquiring the voltage value of the power-supply voltage detected by the A/D converter.

14. The control method according to claim 12,
wherein the imaging element includes:
a pixel portion configured to generate a video signal according to an amount of received light;
an A/D converter configured to perform A/D conversion processing on the video signal to enable output to the control device and to enable detection of the voltage value of the power-supply voltage; and
a memory configured to record a detection result in which the A/D converter detects the voltage value of the power-supply voltage, and
the control method further comprising
acquiring the detection result recorded by the memory in the blanking period of the imaging element as the voltage value of the power-supply voltage.

15. The control method according to claim 12,
wherein the imaging element includes:
a pixel portion configured to generate a video signal according to an amount of received light; and
a superimposition portion configured to output a superimposed signal obtained by superimposing the voltage value of the power-supply voltage supplied from the power source on the video signal, and
the control method further comprising
separating the voltage value of the power-supply voltage from the superimposed signal, and
supply the adjusted voltage value from the power source to the imaging element based on the separated voltage value of the power-supply voltage and on the output voltage value.

* * * * *